(12) United States Patent
Chen et al.

(10) Patent No.: US 10,111,806 B2
(45) Date of Patent: Oct. 30, 2018

(54) DEVICE FOR DELIVERING MIST TO THE HUMAN FACE

(75) Inventors: Xin Chen, Eindhoven (NL); Bjorn Sprengers, Eindhoven (NL); Wan Kei Ricky Ha, Eindhoven (NL); Jiawen Tu, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1172 days.

(21) Appl. No.: 13/581,986

(22) PCT Filed: May 23, 2011

(86) PCT No.: PCT/IB2011/052238
§ 371 (c)(1),
(2), (4) Date: Aug. 30, 2012

(87) PCT Pub. No.: WO2011/148308
PCT Pub. Date: Dec. 1, 2011

(65) Prior Publication Data
US 2013/0160760 A1    Jun. 27, 2013

(30) Foreign Application Priority Data
May 25, 2010    (CN) .......................... 2010 1 0187530

(51) Int. Cl.
*A61H 33/12*     (2006.01)
*A61M 11/00*     (2006.01)
*A61H 35/00*     (2006.01)

(52) U.S. Cl.
CPC .......... *A61H 33/12* (2013.01); *A61H 35/008* (2013.01); *A61M 11/00* (2013.01);
(Continued)

(58) Field of Classification Search
CPC ................. A61H 33/12; A61H 35/008; A61H 2205/022; A61H 2033/021; A61H 33/027;
(Continued)

(56) References Cited

U.S. PATENT DOCUMENTS 2,099,744 A * 11/1937 Lohr ...................... A61H 9/005
                                                       601/17
4,300,556 A * 11/1981 Ochi ...................... A61H 33/12
                                                       604/291

(Continued)

FOREIGN PATENT DOCUMENTS

CN       1636548 A      7/2005
CN     200994992 Y     12/2007
(Continued)

OTHER PUBLICATIONS

Machine Translation of JP 2008295812 provided by the EPO.*

*Primary Examiner* — Joseph Stoklosa
*Assistant Examiner* — Adam Avigan

(57) ABSTRACT

A device (1) for delivering mist to the human face is capable of targeting different kinds of mist to different zones of the human face. To this end, the device (1) comprises different nozzle sets, wherein each of the different nozzle sets serves for letting out a different kind of mist, and wherein each of the different nozzle sets is positioned in a zone (7, 10) of the device (1) corresponding to a zone of the human face to be treated by means of the mist delivered by the nozzle set concerned during operation of the device (1). By having an appropriate number and positioning of the nozzles (2, 3, 4, 5), facial zones can be treated separately, wherein it is possible to realize optimal skin treatment per facial zone.

16 Claims, 4 Drawing Sheets

(52) U.S. Cl.
CPC ............... *A61H 2201/0207* (2013.01); *A61H 2201/0214* (2013.01); *A61H 2201/0228* (2013.01); *A61H 2201/0285* (2013.01)

(58) Field of Classification Search
CPC ............ A61H 33/026; A61H 2033/044; A61H 33/06; A61M 11/00
USPC .................................................. 607/109, 104
See application file for complete search history.

(56) References Cited

U.S. PATENT DOCUMENTS

| | | | | |
|---|---|---|---|---|
| 5,209,227 | A | * | 5/1993 | Deutsch .................. F25B 21/04 607/104 |
| 5,895,418 | A | * | 4/1999 | Saringer .................... A61F 7/00 607/104 |
| 5,938,693 | A | * | 8/1999 | Carminucci .......... A61F 7/0085 607/104 |
| 6,227,456 | B1 | * | 5/2001 | Colman ................ E03C 1/0404 239/1 |
| 6,282,369 | B1 | * | 8/2001 | Maier et al. .................. 392/403 |
| 6,623,511 | B1 | * | 9/2003 | Daffer ................... A61F 7/0053 128/898 |
| 7,000,682 | B2 | * | 2/2006 | Chambers ............. A41D 13/005 165/46 |
| 2005/0061896 | A1 | * | 3/2005 | Luettgen ............... B05B 1/1654 239/449 |
| 2005/0211245 | A1 | * | 9/2005 | Smaldone .............. A61M 11/06 128/204.18 |
| 2006/0207013 | A1 | * | 9/2006 | Deboer et al. .................... 4/601 |
| 2011/0162528 | A1 | * | 7/2011 | Yamaguchi ............... A01N 3/00 96/251 |
| 2013/0053737 | A1 | * | 2/2013 | Scerbo ........................... 601/46 |
| 2013/0119154 | A1 | * | 5/2013 | Sawyer ......................... 239/289 |
| 2013/0150757 | A1 | * | 6/2013 | Faredoun ................ B05B 1/24 601/17 |
| 2014/0035331 | A1 | * | 2/2014 | Sawyer .................... 297/180.15 |

FOREIGN PATENT DOCUMENTS

| | | | |
|---|---|---|---|
| CN | 101588779 | A | 11/2009 |
| EP | 2146152 | A1 | 1/2010 |
| GB | 2056852 | A | 3/1981 |
| JP | 2003000672 | A | 1/2003 |
| JP | 2008295812 | A * | 12/2008 ............. A61H 33/10 |
| WO | 20000066063 | A1 | 11/2000 |
| WO | 2008149722 | A1 | 12/2008 |
| WO | 2008149723 | A1 | 12/2008 |
| WO | 2009066707 | A1 | 5/2009 |

* cited by examiner

DEVICE FOR DELIVERING MIST TO THE HUMAN FACE

FIELD OF THE INVENTION

The present invention relates to a device for delivering mist to the human face, comprising an outlet area in which a number of nozzles are arranged. In the following, for the sake of clarity, a device as mentioned will be denoted as facial mister.

BACKGROUND OF THE INVENTION

A facial mister is a beauty device which is used for treating the skin of the face in order to achieve useful effects like cleansing of the skin and/or refreshment of the skin. A facial mister which is adapted to generate different kinds of mist is known. For example, JP 2008-295467 discloses a hot and cold misting apparatus comprising a cold mist producing part and a hot mist producing part, and two nozzles for discharging the cold mist and the hot mist. The two kinds of mist can be discharged simultaneously if so desired. A microcomputer is provided for controlling the discharge process, which can also involve an alternating use of the two nozzles, for example.

On the basis of the fact that the discharge of the two kinds of mist can be controlled, a user of the known facial mister can choose any type of treatment of the skin of the face. However, the known facial mister does not help in obtaining a most effective treatment.

SUMMARY OF THE INVENTION

It is an object of the present invention to improve the known device for delivering mist to the human face, in order to have a most effective treatment of the skin of the face. This object is achieved by means of a device of the kind mentioned in the opening paragraph, in which the outlet area comprises a first zone, which covers at least an elongated central portion of the outlet area that has a main vertical orientation in the outlet area, and a second zone excluding the first zone, which covers portions of the outlet area adjoining each main side of said central portion, the device further comprising a first nozzle set having at least one nozzle for letting out mist of a first kind and a second nozzle set having at least one nozzle for letting out mist of a second kind different from the first kind, wherein each nozzle of the first nozzle set is present in the first zone of the outlet area and each nozzle of the second nozzle set is present in the second zone of the outlet area, whereby the device is adapted to target the first and second kinds of mist to respective different zones of the human face.

The present invention provides an insight that improved results of treatment with various kinds of mist are obtained when the various kinds of mist are used for treating specific zones of the human face, i.e. when one kind of mist is used for treating one facial zone, another kind of mist is used for treating another facial zone, etc. It has been found that different areas of the facial skin have different requirements when it comes to a treatment with the help of mist. By grouping the nozzles of the facial mister together in certain nozzle sets, wherein the at least one nozzle of one nozzle set is used for emitting a different kind of mist than the at least one nozzle of another nozzle set, and by having the nozzle sets positioned in appropriate zones, a situation in which each zone of the skin to be treated can be provided with a most appropriate kind of mist is realized.

A difference between kinds of mist can be found in one or more of various factors, including temperature, density, intensity and particle size. Each nozzle set comprises at least one nozzle, wherein the design of the at least one nozzle may be chosen freely, and may be optimized per set. Factors relating to the design of the nozzles, which can be adapted to the intended use of the nozzles in an appropriate nozzle set, include shape, size and pointing direction, i.e. direction in which the emission of the mist can take place. Examples of the shape of the nozzles include a circle, an ellipse, a square, and a rectangle. The pointing direction can be perpendicular to a panel for supporting the nozzles of the facial mister, which panel may define the outlet area of the facial mister, but it is also possible for the pointing direction to be inclined at a certain angle with respect to the panel as mentioned.

Within the scope of the present invention, the facial mister can be adapted to subject two or more facial zones to different treatments by targeting different kinds of mist towards those zones. In many cases, two main zones are distinguished in the human face, namely a so-called T-zone and a so-called U-zone. The T-zone comprises the forehead, the nose, and usually also the chin, whereas the U-zone comprises both cheeks. In a facial mister according to the present invention, which is suitable for supplying one kind of mist to the T-zone and another kind of mist to the U-zone of the human face, the first zone of the outlet area, i.e. the zone covering at least an elongated central portion of the outlet area that has a main vertical orientation in the outlet area is T-shaped, and is thereby a zone of the outlet area corresponding to the T-zone of the human face, and the second zone of the outlet area, i.e. the zone covering portions of the outlet area adjoining each main side of said central portion of the outlet area is U-shaped, and is thereby a zone of the outlet area corresponding to the U-zone of the human face, wherein the T-shape of the first zone of the outlet area is orientated such as to stand on a base of the U-shape of the second zone of the outlet area. In such a case, the nozzle sets may differ as far as the temperature of the mist which is emitted by the nozzles of the various nozzle sets is concerned, for example. In particular, the facial mister according to the present invention may comprise means for generating mist at a relatively low temperature, and means for generating mist at a relatively high temperature, wherein the nozzle set which is positioned in a zone of the outlet area corresponding to the T-zone of the human face is connected to the first means, and wherein the nozzle set which is positioned in a zone of the outlet area corresponding to the U-zone of the human face is connected to the latter means. On the basis of this design of the facial mister, the T-zone can be treated by relatively cold mist, and the U-zone can be treated by relatively hot mist. All that a user needs to do is to put his/her face in front of the nozzle panel, at a correct position with respect to the nozzle panel. When the facial mister is activated, the correct treatments are then automatically performed at the intended facial zones, which yields improved skin treatment results. In any case, the results are much better than when only one type of nozzles is used for emitting mist, and are also much better than when at least two types of nozzles are used, but not properly positioned, i.e. not accurately positioned in zones of the outlet area corresponding to the zones of the skin to be treated.

For the sake of clarity, it is noted that in the following, the term "central portion of the outlet area" will be used to denote the elongated central portion of the outlet area that has a main vertical orientation in the outlet area. The main sides of the central portion are the sides having the main vertical orientation of the central portion. Consequently, the central portion has two main sides, and these are the sides which are each adjoined by a portion of the outlet area which is covered by the second zone of the outlet area as defined in the foregoing.

The nozzle set which is positioned in the first zone of the outlet area as defined in the foregoing may comprise a single nozzle which is located at a position corresponding to a position of a central portion of the forehead. If there are two nozzles in the first zone, one nozzle may be located at a position corresponding to the position of the chin and the other nozzle may be located at the position corresponding to the position of the central portion of the forehead. For the sake of completeness, it is noted that in many practical cases, the central portion of the outlet area extends over at least a substantial portion of the height of the outlet area, possibly over the entire height. Furthermore, it is noted that the main vertical orientation of this portion relates to its positioning in the outlet area, in which a bottom side and a top side can be discerned, wherein this portion extends between the sides as mentioned, perpendicular to a horizontal direction, assuming a normal, operational orientation of the facial mister. The bottom side is associated with a chin side of the human face, and the top side is associated with a forehead side of the human face. Consequently, in the normal operational orientation of the facial mister, the bottom side of the outlet area is at a lower level than the top side of the outlet area. For the sake of completeness, it is noted that the outlet area may have an inclined orientation with respect to the vertical. In view of that fact, the central portion is not defined as having a vertical orientation in a general sense, but as having a vertical orientation in the outlet area.

Preferably, the nozzle set which is positioned in the second zone of the outlet area comprises at least two nozzles, wherein at least one nozzle is arranged at one side of the central portion, and wherein at least another nozzle is arranged at another side of the central portion, such that there is a nozzle for each cheek.

As has been mentioned in the foregoing, the mist which is emitted by the various nozzle sets may differ in one or more aspects. One aspect is the temperature of the mist, and the device according to the present invention may comprise means for generating mist at a relatively low temperature, and means for generating mist at a relatively high temperature, wherein at least one of the nozzle sets is connected to the first means, and wherein at least another one of the nozzle sets is connected to the latter means. In particular, the nozzle set which is present in the first zone of the outlet area may be connected to the first means, while the nozzle set which is present in the second zone of the outlet area may be connected to the latter means.

The means for realizing a desired temperature of the mist may be designed in any appropriate way. For example, the means for generating mist at a relatively low temperature may comprise a tank for containing a fluid to be used in the process of making mist, a nebulizer arranged at a side of the tank which is a bottom side in a normal orientation of the facial mister, and a cooler such as a Peltier cooler, and the means for generating mist at a relatively high temperature may comprise a tank for containing a fluid to be used in the process of making mist, a nebulizer arranged at a side of the tank which is a bottom side in a normal orientation of the facial mister, and a heater such as a PTC (Positive Temperature Coefficient) heater. The nebulizers as mentioned may comprise ultrasonic nebulizers known per se, for example. For the sake of completeness, in respect of the means for generating mist at a relatively low temperature, it is noted that it is not necessary to have a cooler, as the relatively cold mist may be acceptable to a user of the facial mister as long as the mist is not subjected to any heating process. Furthermore, it has been found that the nebulizer may cause the mist temperature to be lower than room temperature.

The above-described and other aspects of the present invention will be apparent from and elucidated with reference to the following detailed description of a facial mister comprising two nozzle sets, wherein one nozzle set is adapted to emit relatively cold mist towards the T-zone of the face of a user, and wherein another nozzle set is adapted to emit relatively hot mist towards the U-zone of the face of a user.

BRIEF DESCRIPTION OF THE DRAWINGS

The present invention will now be explained in greater detail with reference to the Figures, in which equal or similar parts are indicated by the same reference signs, and in which.

DETAILED DESCRIPTION OF EMBODIMENTS

Figure 1:
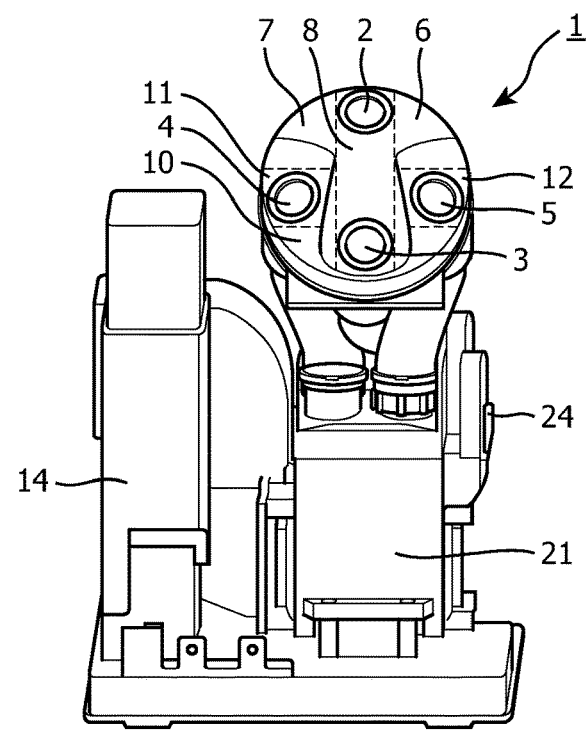
FIG. 1 diagrammatically shows a front view of a facial mister according to the present invention.
Figure 2:
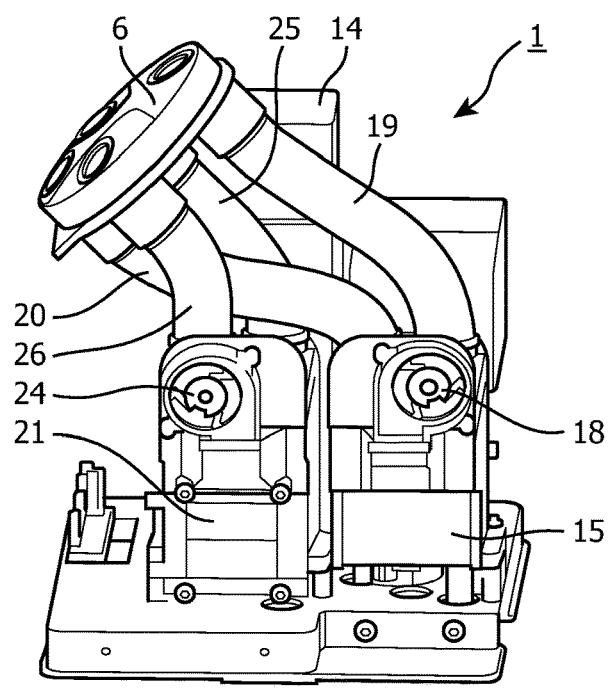
FIG. 2 diagrammatically shows a side view of the facial mister.
Figure 3:
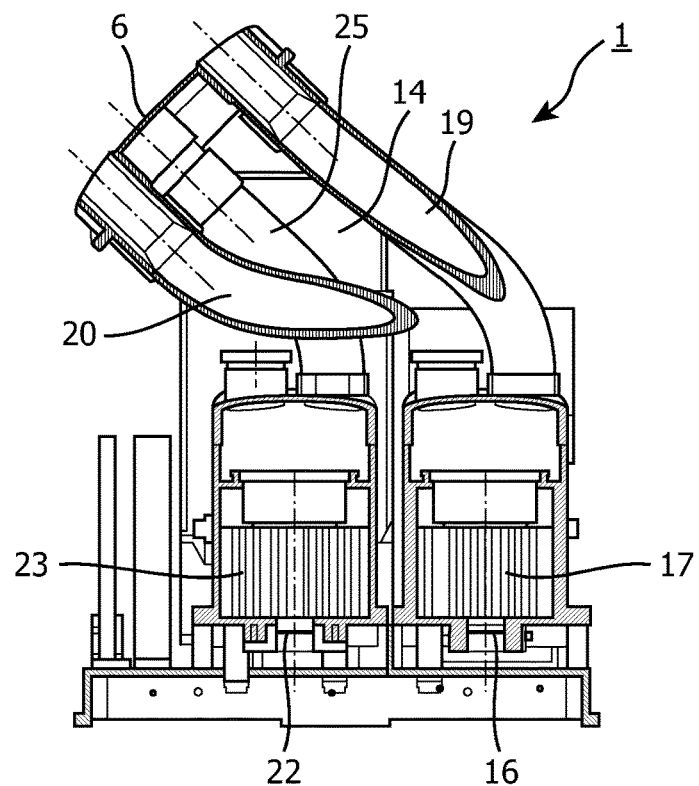
FIG. 3 diagrammatically shows a view of a cross-section through the facial mister.

FIGS. 1-3 show different views of a facial mister 1 according to the present invention. For the sake of completeness, it is noted that the facial mister 1 which is shown in the Figures and which will be described hereinafter is only one example existing within the scope of the present invention, and that other embodiments of the facial mister are possible.

In general, a facial mister is adapted to emit mist through one or more nozzles. A user of the facial mister is supposed to put his/her face in front of an outlet area of the facial mister, so that the mist can reach the facial skin of the user and perform a desired treatment on the skin, such as a cleansing treatment and/or a soothing treatment. In practical cases, the outlet area comprises a nozzle panel, which serves for supporting the at least one nozzle for letting out the mist.

According to the present invention, a facial mister is adapted to emit at least two kinds of mist, wherein the nozzles for emitting the different kinds of mist are positioned in different zones. Each of the zones on the facial mister corresponds to a zone of the human face, wherein a nozzle set for treating a specific zone is positioned in a corresponding zone on the facial mister.

Figure 4:
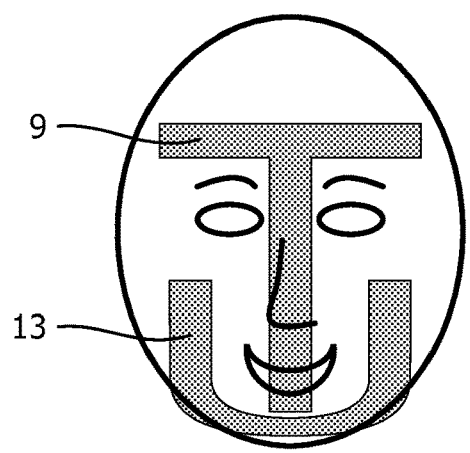
FIG. 4 illustrates the positioning of the T-zone and the U-zone on the human face.
Figure 6:
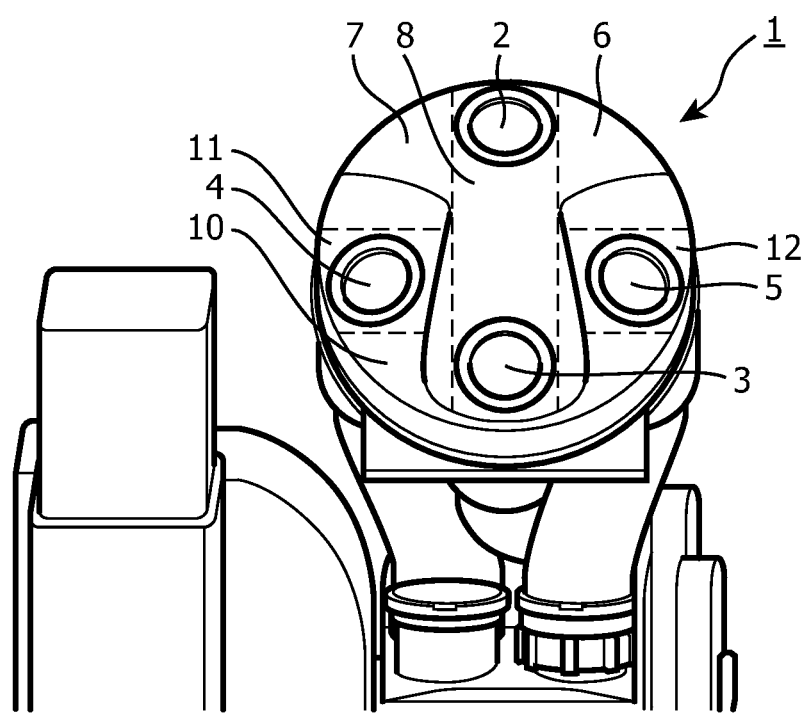
FIG. 6 shows an enlarged view of a portion of FIG. 1.

In the shown example, the facial mister 1 is adapted to emit relatively cold mist and relatively hot mist, through nozzles 2, 3, 4, 5 which are arranged in a nozzle panel 6, and which are grouped in two different sets. In particular, one set of nozzles 2, 3 is located in a zone 7 which covers an elongated, vertically orientated central portion 8 of the nozzle panel 6, and which corresponds to the so-called T-zone 9 on the human face, and another set of nozzles 4, 5 is located in a zone 10 which covers portions 11, 12 of the nozzle panel 6 which are present on each main side of the central portion 8 of the nozzle panel 6, and which corresponds to the so-called U-zone 13 on the human face. The positioning of the zones 9, 13 on the human face as mentioned is illustrated in FIG. 4. In FIG. 1, the positioning of the central portion 8 of the nozzle panel 6 and the portions 11, 12 of the nozzle panel 6 which are present on each main side of said central portion 8 is indicated by means of dashed lines. For the sake of clarity, FIG. 6 shows a portion of FIG. 1, in an enlarged view, so that the various portions 8, 11, 12 of the nozzle panel 6 and the zones 7, 10 are clearly distinguishable.

The nozzles 2, 3 for delivering mist which is intended to reach the T-zone 9 are positioned at the end of a line for supplying relatively cold mist, and the nozzles 4, 5 for delivering mist which is intended to reach the U-zone 13 are positioned at the end of a line for supplying relatively hot mist. The various kinds of mist are made on the basis of water. The facial mister 1 may comprise a single container 14 for containing water and supplying water to the two lines as mentioned, as is the case with the shown example, which does not alter the fact that it is possible to apply more containers, or to have a connection to a tap or the like for a continuous supply of water to the facial mister 1, for example. In the following, for the sake of clarity, the container 14 as mentioned will be referred to as water supply container 14.

The line for supplying relatively cold mist may be designed in any suitable way. FIGS. 1-3 illustrate an embodiment in which the line as mentioned comprises a cold water tank 15 which is connected to the water supply container 14, wherein an ultrasonic nebulizer 16 is arranged at a bottom of the cold water tank 15, and wherein a Peltier cooler is arranged at a side of the cold water tank 15. A metal heat sink 17 with a plurality of fins is in contact with the Peltier cooler, and is used for more effective cooling of water. Furthermore, the line for supplying relatively cold mist comprises a nebulization fan 18 and tubes 19, 20 for delivering the mist to the nozzles 2, 3 of the T-zone 7 of the nozzle panel 6.

The line for supplying relatively hot mist may be designed in any suitable way as well. FIGS. 1-3 illustrate an embodiment in which the line as mentioned comprises a warm water tank 21 which is connected to the water supply container 14, wherein an ultrasonic nebulizer 22 is arranged at a bottom of the warm water tank 21, and wherein heaters such as PTC heaters are arranged at a side of the warm water tank 21. A metal heat sink 23 with a plurality of fins is in contact with the PTC heaters, and is used for more effective heating of water. Furthermore, the line for supplying relatively hot mist comprises a nebulization fan 24 and tubes 25, 26 for delivering the mist to the nozzles 4, 5 of the U-zone 10 of the nozzle panel 6.

Preferably, for the purpose of controlling the operation of the facial mister 1 in such a way that a user's desires are met, the facial mister 1 is equipped with a suitable controller and user interface. A closed control loop is formed to control the operation of the facial mister 1. Temperature sensors are attached to both the cold water tank 15 and the warm water tank 21 in order to ensure that nebulization only starts when a desired water temperature is achieved. Among other things, the controller is connected to the following components of the facial mister 1:

a temperature sensor of the cold water tank 15;
a nebulizer driver of the cold water tank 15;
the nebulization fan 18 of the line for supplying relatively cold mist;
a fan for cooling the Peltier cooler;
means for supplying power to the Peltier cooler;
a temperature sensor of the warm water tank 21;
a nebulizer driver of the warm water tank 21;
the nebulization fan 24 of the line for supplying relatively hot mist; and
means for supplying power to the PTC heaters.

The facial mister 1 according to the present invention is capable of restoring the natural water and oil balance of the skin of the human face. Through different nozzles 2, 3, 4, 5, mist which is directed to the T-zone 9 of the human face is separated from mist which is directed to the U-zone 13 of the human face. At the same time, the mist is conditioned for these zones 9, 13 specifically. For example, the temperature, the density, and the intensity of the mist can be different for the T-zone 9 and the U-zone 13.

The facial mister 1 offers many possibilities of supplying mist to the human face. In the first place, it is possible to only generate relatively hot mist, and deliver this mist to a user's face through the nozzles 4, 5 of the U-zone 10 of the nozzle panel 6. In the second place, it is possible to only generate relatively cold mist, and deliver this mist to a user's face through the nozzles 2, 3 of the T-zone 7 of the nozzle panel 6. The relatively cold mist can be obtained by using the Peltier cooler, but this is not necessary if the user does not require the temperature of the mist to be as low as possible. In the third place, it is possible to generate both relatively hot mist and relatively cold mist, and deliver the relatively hot mist to a user's face through the nozzles 4, 5 of the U-zone 10 of the nozzle panel 6, and simultaneously deliver the relatively cold mist to the user's face through the nozzles 2, 3 of the T-zone 7 of the nozzle panel 6.

Furthermore, relatively cold mist can be delivered to a user's face through the nozzles 4, 5 of the U-zone 10 of the nozzle panel 6 as long as the heaters are not activated or still in the process of heating up the water in the warm water tank 21. In that case, it is possible to use all nozzles 2, 3, 4, 5, and cool the entire face of a user. Also, the entire face of a user can be heated by realizing a relatively high density of relatively hot mist which is emitted through the nozzles 4, 5 of the U-zone 10 of the nozzle panel 6.

The fact that the facial mister 1 according to the present invention is multifunctional is very advantageous for achieving desired effects of facial skin treatment. A special feature of the facial mister 1 is the fact that different kinds of mist are targeted at different facial zones 9, 13. In this way, the treatment process can take place in an optimal manner, as different requirements pertaining to different facial zones 9, 13 can be met separately.

Figure 5:
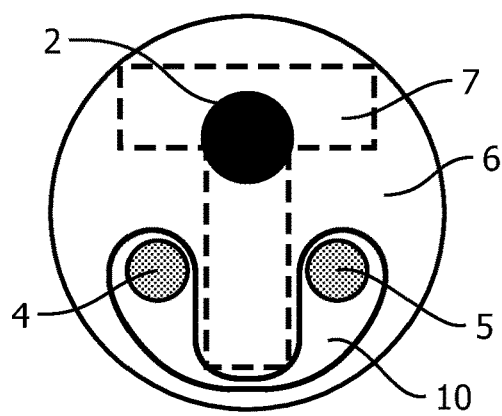
FIG. 5 diagrammatically shows three different options of an arrangement of nozzles in the facial mister.
Figure 5:
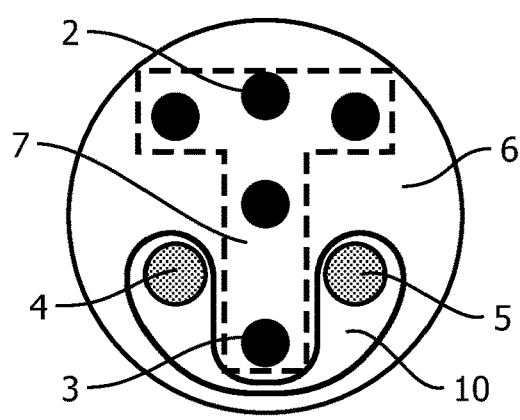
Figure 5:
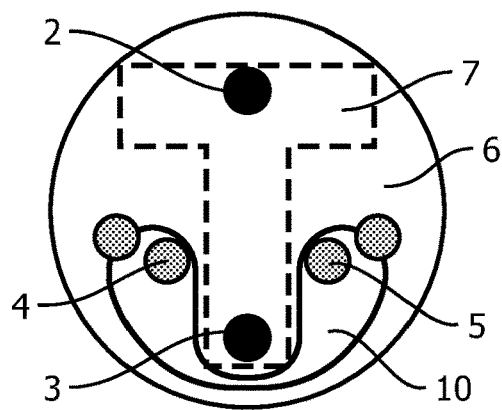

The nozzle panel 6 can be designed in any appropriate way, with at least two zones 7, 10, and the number and the positioning of the nozzles 2, 3, 4, 5 per zone 7, 10 can be chosen such as to yield optimal results of the skin treatment to be performed by means of the mist to be emitted by the nozzles 2, 3, 4, 5. In the shown example, one nozzle set is positioned in a T-zone 7 of the nozzle panel 6, and another nozzle set is positioned in a U-zone 10 of the nozzle panel 6. In particular, in the facial mister 1 shown in FIGS. 1-3, two nozzles 2, 3 are arranged in the T-zone 7, and two nozzles 4, 5 are arranged in the U-zone 10. FIG. 5 illustrates a number of alternatives of the number and the positioning of the nozzles in the zones 7, 10 as mentioned. In the first place, it is possible to have only one nozzle 2 at the end of the line for delivering relatively cold mist, which nozzle 2 may be positioned at a top side of the T-shape of the T-zone 7. In the second place, it is possible to have more than two nozzles 2, 3 at the end of the line for delivering relatively cold mist, wherein the nozzles may be positioned such as to be more or less evenly distributed over the T-shape of the T-zone 7. In the third place, it is possible to have more than two nozzles 4, 5 at the end of the line for delivering relatively hot mist, wherein the nozzles may be positioned at the end of both legs of the U-shape of the U-zone 10.

In any case, the configuration of the nozzles 2, 3, 4, 5 can be chosen such that a more or less separated treatment of different facial zones 9, 13 is realized during operation of the facial mister 1, which is the intended effect of the present invention.

It will be clear to a person skilled in the art that the scope of the present invention is not limited to the examples discussed in the foregoing, but that several amendments and modifications thereof are possible without deviating from the scope of the present invention as defined in the attached claims. While the present invention has been illustrated and described in detail in the Figures and the description, such illustration and description are to be considered illustrative or exemplary only, and not restrictive. The present invention is not limited to the disclosed embodiments.

Variations to the disclosed embodiments can be understood and effected by a person skilled in the art in practicing the claimed invention, from a study of the Figures, the description and the attached claims. In the claims, the word "comprising" does not exclude other steps or elements, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope of the present invention.

For the sake of completeness, it is noted that a suitable fluid other than water may be used for the purpose of making the mist which is used in the process for treating the facial skin by means of the facial mister 1 according to the present invention.

The present invention can be summarized as follows. A device 1 for delivering mist to the human face is adapted to generate different kinds of mist, and is capable of targeting the different kinds of mist to different zones 9, 13 of the human face. To this end, the device 1 comprises different nozzle sets, wherein each of the different nozzle sets serves for letting out another kind of mist, and wherein each of the different nozzle sets is positioned in a zone 7, 10 of the device 1 corresponding to a zone 9, 13 of the human face to be treated by means of the mist delivered by the nozzle set concerned during operation of the device 1. The number of nozzles 2, 3, 4, 5 of a nozzle set is at least one, and by having an appropriate number and positioning of the nozzles 2, 3, 4, 5, grouped together in various nozzle sets as mentioned, facial zones 9, 13 can be treated separately, wherein it is possible to realize optimal skin treatment per facial zone 9, 13. In a practical embodiment, one nozzle set is present in the device 1 for supplying mist to a T-zone 9 of the human face, and another nozzle set is present in the device 1 for supplying mist to a U-zone 13 of the human face.

The invention claimed is:

1. A device for delivering mist to a person's face when placed in a predetermined operational orientation on the face, said device comprising:
   a. a nozzle panel defining an outlet area including separate first and second zones, wherein the second zone excludes the first zone, (i) the first zone including an elongated central portion of the outlet area of the nozzle panel, having a principal vertical orientation, and configured to limit delivery of mist to a corresponding area of a person's face that includes forehead, nose and chin, and (ii) the second zone including first and second portions of the outlet area of the nozzle panel, respectively adjoining principal sides of the elongated central portion of the first zone, and configured to limit delivery of mist to corresponding areas on left and right sides of the person's face that include left and right cheeks;
   b. at least one nozzle disposed within the nozzle panel in the first zone and adapted to emit a first nebulized water mist having a first temperature via the elongated central portion of the outlet area of the nozzle panel in the first zone, whereby delivery of the first mist is limited to the corresponding area of the person's face; and
   c. at least second and third nozzles disposed within the nozzle panel in the second zone and adapted to emit, simultaneously with the emitting of the first mist, respective second and third nebulized water mists via the first and second portions of the outlet area of the nozzle panel in the second zone, whereby delivery of the second and third mists is limited to the corresponding areas on the left and right sides of the persons' face, said second and third nozzles being adapted to simultaneously emit the respective second and third mists at a second temperature that is higher than the first temperature.

2. The device for delivering mist to a person's face according to claim 1 where the first zone has a T-shaped configuration and where said device includes a plurality of nozzles arranged in said T-shaped configuration.

3. The device for delivering mist to a person's face according to claim 2 where the second zone has a U-shaped configuration and where the T-shape of the first zone is oriented so as to stand on a base of the U-shape of the second zone.

4. The device for delivering mist to a person's face according to claim 1 and further including
   a) a first liquid source, for use in making and supplying the first mist having the first temperature, coupled to the at least one nozzle disposed in the first zone for emitting the first mist having the first temperature; and
   b) a second liquid source, for use in making and supplying at least one of the second and third mists having the second temperature, coupled to at least one of the second and third nozzles disposed in the second zone for emitting the respective mist having the second temperature.

5. The device for delivering mist to a person's face according to claim 4 where the first liquid source includes a first liquid tank.

6. The device for delivering mist to a person's face according to claim 5 and further including a cooling device thermally coupled to the first liquid tank for controllably cooling liquid for use in making the first mist, supplied from the first liquid tank.

7. The device for delivering mist to a person's face according to claim 6 where the cooling device comprises a Peltier cooler.

8. The device for delivering mist to a person's face according to claim 5 and including an ultrasonic nebulizer coupled to the first liquid tank.

9. The device for delivering mist to a person's face according to claim 4 where the second liquid source includes a second liquid tank.

10. The device for delivering mist to a person's face according to claim 9 and further including a heating device for controllably heating liquid for use in making the second mist, supplied from the second liquid tank.

11. The device for delivering mist to a person's face according to claim 9 and including an ultrasonic nebulizer coupled to the second liquid tank.

12. The device for delivering mist to a person's face according to claim 1 where each of the first, second and third mists emitted has at least one of a specific temperature, density, intensity and particle size.

13. The device for delivering mist to a person's face according to claim 1 and including a plurality of nozzles disposed in each of the first and second portions of the second zone.

14. The device according to claim 1 where the first zone of the outlet area is configured to limit delivery of mist to at least one of a person's forehead, nose and chin.

15. The device according to claim 1 where the second zone of the outlet area is configured to limit delivery of mist to at least one of a person's left and right cheeks.

16. A device for delivering mist to a person's face when placed in a predetermined operational orientation on the face, said device comprising:
   a. a nozzle panel defining an outlet area including separate first and second zones, wherein the second zone excludes the first zone, (i) the first zone including an elongated central portion of the outlet area of the nozzle panel, having a principal vertical orientation, and configured to limit delivery of mist to a corresponding area of a person's face that includes forehead, nose and chin, and (ii) the second zone including first and second portions of the outlet area of the nozzle panel, respectively adjoining principal sides of the elongated central portion of the first zone, and configured to limit delivery of mist to corresponding areas on left and right sides of the person's face that include left and right cheeks;
   b. at least a first nozzle disposed within the nozzle panel in the first zone and adapted to emit a first nebulized water mist having a first temperature via the elongated central portion of the outlet area of the nozzle panel in the first zone, whereby delivery of the first mist is limited to the corresponding area of the person's face;
   c. at least second and third nozzles disposed within the nozzle panel in the second zone and adapted to emit second and third nebulized water mists via the first and second portions of the outlet area of the nozzle panel in the second zone, whereby delivery of the second and third mists is limited to the corresponding areas on the left and right sides of the persons' face, simultaneously with emitting of the first mist, said second and third mists having a temperature that is higher than the first temperature; and
   d. separate liquid sources for use in making and supplying said first mist having said first temperature and said second and third mists having said second temperature to respective ones of the nozzles emitting the first and second and third mists.

\* \* \* \* \*